United States Patent
Bilbe et al.

(10) Patent No.: US 7,638,510 B2
(45) Date of Patent: Dec. 29, 2009

(54) USE OF S-10-HYDROXY-10,11-DIHYDRO-CARBAMAZEPINE FOR THE TREATMENT OF ANXIETY AND BIPOLAR DISORDERS

(75) Inventors: Graeme Bilbe, Neuchatel (CH); John F. Cryan, Basel (CH); Conrad Gentsch, Binningen (CH); Kevin Hall McAllister, Buschwiller (FR); Markus Schmutz, Schoenenbuch (CH); Annick Vassout, Sierentz (FR)

(73) Assignee: Novartis AG, Basel (CH)

( * ) Notice: Subject to any disclaimer, the term of this patent is extended or adjusted under 35 U.S.C. 154(b) by 632 days.

(21) Appl. No.: 10/545,411

(22) PCT Filed: Feb. 16, 2004

(86) PCT No.: PCT/EP2004/001452

§ 371 (c)(1), (2), (4) Date: Aug. 12, 2005

(87) PCT Pub. No.: WO2004/071152

PCT Pub. Date: Aug. 26, 2004

(65) Prior Publication Data

US 2006/0194791 A1     Aug. 31, 2006

(30) Foreign Application Priority Data

| Feb. 17, 2003 | (GB) | ................... 0303613.4 |
| Feb. 17, 2003 | (GB) | ................... 0303614.2 |
| Mar. 28, 2003 | (GB) | ................... 0307278.2 |
| Mar. 28, 2003 | (GB) | ................... 0307281.6 |

(51) Int. Cl.
- *A01N 43/46* (2006.01)
- *A01N 43/00* (2006.01)
- *A61K 31/55* (2006.01)
- *A61K 31/5517* (2006.01)

(52) U.S. Cl. .................... 514/217; 424/474

(58) Field of Classification Search ............... None
See application file for complete search history.

(56) References Cited

U.S. PATENT DOCUMENTS

2005/0004102 A1*  1/2005  Schmutz ............ 514/217

OTHER PUBLICATIONS

Volosov et al, "Enantioselective Pharmacokinetics of 10-Hydroxycarbazepine After Oral Administration of Oxcarbazepine to Healthy Chinese Subjects", Clinical Pharmacology and Therapeutics, vol. 66, No. 6pp. 547-553, (1999).*

* cited by examiner

*Primary Examiner*—Ardin Marschel
*Assistant Examiner*—Amy A Lewis
(74) *Attorney, Agent, or Firm*—Daniel Woods; Cozette M. McAvoy

(57) ABSTRACT

The present invention relates to the use of a racemate of the compound of formula (1) consisting of at least 85% S-enantiomer and not more than 15% R-enantiomer or of pharmaceutically acceptable salts of said racemate or of the S-enantiomer of formula I or of pharmaceutically acceptable salts of said enantiomer for the treatment of anxiety or other psychiatric disorders with underlying anxiety symptomatologies or for the treatment of affective and attention disorders; pharmaceutical compositions for that purpose and packages comprising said pharmaceutical compositions together with instructions for the use of said compositions for the treatment of anxiety or other psychiatric disorders with underlying anxiety symptomatologies or of affective and attention disorders.

(I)

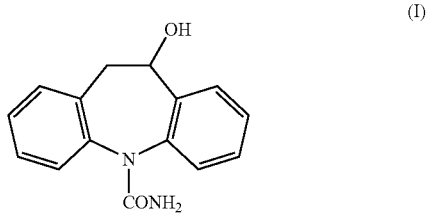

7 Claims, No Drawings

USE OF S-10-HYDROXY-10,11-DIHYDRO-CARBAMAZEPINE FOR THE TREATMENT OF ANXIETY AND BIPOLAR DISORDERS

The present invention relates to new pharmaceutical uses of a carbamazepine derivative.

More particularly the present invention relates to new pharmaceutical uses for a racemate of the carbamazepine derivative of formula I

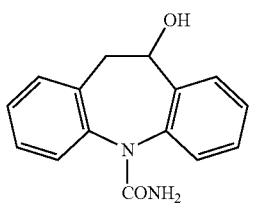

and its pharmaceutically acceptable salts.

Racemic licarbazepine (MHD, formula I, 10-hydroxy-10, 11-dihydro-carbamazepine), the main metabolite of the anti-epileptic drug oxcarbazepine (Trileptal®), is well known from the literature [see for example Schuetz H. et al., Xenobiotica (GB), 16(8), 769-778 (1986)] and can be prepared synthetically starting from oxcarbazepine according to conventional methods. It was demonstrated that the racemate (formula I) and both of its pure enantiomers are of equal efficacy against epilepsy.

In accordance with the present invention, it was now surprisingly found that the S-enantiomer of the compound of formula I is substantially more efficacious than the R-enantiomer in the prevention and the treatment of affective and attention disorders, anxiety and other psychiatric disorders with underlying anxiety symptomatologies.

Hence, the present invention pertains to the use of the racemate of the compound of formula I consisting of at least 85% S-enantiomer and not more than 15% R-enantiomer, hereafter referred to as "the racemate", the use of the pure S-enantiomer, and to the use of pharmaceutically acceptable salts of said racemate or enantiomer, for the treatment of affective and attention disorders, anxiety and other psychiatric disorders with underlying anxiety symptomatologies.

One embodiment of the present invention pertains to the use of the S-enantiomer of the compound of formula I or of a pharmaceutically acceptable salt thereof for the treatment of affective and attention disorders, anxiety and other psychiatric disorders with underlying anxiety symptomatologies.

The term "affective and attention disorders" as used herein includes, but is not restricted to depression or other psychiatric disorders like uni- and bi-polar disorders, e.g. manic-depressive psychoses, extreme psychotic states, e.g. mania, pre-menstrual dysphoric disorder, post-partum depression, post-menopausal depression, neurodegeneration-related depressive symptoms and depression.

The term "anxiety or other psychiatric disorders with underlying anxiety symptomatologies" as used herein includes, but is not restricted to general anxiety disorders, social anxiety disorders, post traumatic stress disorder, obsessive compulsive disorder, panic and anxiety occurring following cessation of psychostimulant intake.

The suitability of the agents of the invention for the treatment of affective and attention disorders can be evidenced, for example, in tests suitable for detecting drugs reversing psycho-motor stimulatory effects. In particular, it can be evidenced in the Vogel conflict test described in the Example below. The person skilled in the pertinent art is fully enabled to select further relevant test models to prove such activity. The usefulness of the agents of the invention in the treatment of the above-mentioned disorders can be confirmed in suitable clinical studies. Suitable clinical studies are in particular randomized, double-blind, placebo-controlled, parallel studies in bi-polar mood disorders patients or patients having psychiatric disorders with underlying anxiety symptomatologies.

The Vogel conflict test described in the Examples below is the standard test to detect psychiatric, mainly anxiolytic and antidepressant drug action since various classes of anxiolytic and antidepressant drugs are effective in this test and since there is a high co-morbidity between anxiety states and other psychiatric, e.g., depression disorders. The very surprising specific and high efficacy of, above all, the S-enantiomer in this test is therefore indicative of drug activity in anxiety, depression and other psychiatric disorders as defined above.

The obtained results from the Vogel conflict test clearly demonstrate that the R-enantiomer at the highest dose used (200 mg/kg) is less efficacious than the S-enantiomer at the lowest dose used (50 mg/kg), whereas the potency/efficacy ratio of the racemate is between that of the R- and S-enantiomers. This finding is very surprising in the light of the anticonvulsant findings where all 3 compounds are equipotent, i.e., their potency is within a factor of less than 2.

For the treatment of the diseases mentioned above, appropriate dosage will of course vary depending upon, for example, the ratio of the different enantiomers, the host, the disease to be treated, the mode of administration and the nature and severity of the condition being treated. However, in general, satisfactory results in animals are indicated to be obtained at a daily dosage of from about 1 to 300 mg/kg animal body weight of the racemate or the S-enantiomer. In larger mammals, for example humans, an indicated daily dosage of the racemate or the S-enantiomer is in the range from about 10 to about 3000 mg of a compound according to the invention, conveniently administered, for example, in divided doses up to four times a day.

The racemate or the enantiomer may be administered in any usual manner, e.g. orally, for example in the form of tablets or capsules, or parenterally, for example in the form of injection solutions or suspensions.

The present invention also provides pharmaceutical compositions comprising the racemate of the compound of formula I or pharmaceutically acceptable salts of said racemate consisting of at least 51% S-enantiomer and not more than 49% R-enantiomer, preferably at least 85% S-enantiomer and not more than 15% R-enantiomer, or the S-enantiomer, in association with at least one pharmaceutical carrier or diluent, in particular, for the use in the treatment of affective and attention disorders or anxiety or other psychiatric disorders. with underlying anxiety symptomatologies. Such compositions may be manufactured in a conventional manner.

Unit dosage forms may contain for example from about 2.5 mg to about 1000 mg of the racemate or the S-enantiomer.

The invention further relates to the use of a racemate or the S-enantiomer of the compound of formula I or of pharmaceutically acceptable salts of said racemate or enantiomer for the manufacture of a pharmaceutical composition for the treatment of affective and attention disorders or anxiety or other psychiatric disorders with underlying anxiety symptomatologies.

The invention further provides a method for the treatment of affective and attention disorders in a subject in need of such treatment, which comprises administering to said subject a therapeutically effective amount of a racemate according to the invention or of the S-enantiomer or of a pharmaceutically acceptable salt of said racemate or enantiomer.

The invention further provides a method for the treatment of anxiety or other psychiatric disorders with underlying anxiety symptomatologies in a subject in need of such treatment, which comprises administering to said subject a therapeutically effective amount of a racemate according to the invention or of the S-enantiomer or of a pharmaceutically acceptable salt of said racemate or enantiomer.

One preferred embodiment of the invention relates to the use of the racemate of the invention or the S-enantiomer in the treatment of bipolar mood disorders.

Furthermore, the present invention provides a package comprising a pharmaceutical composition comprising the racemate of the compound of formula I consisting of at least 51% S-enantiomer and not more than 49% R-enantiomer, preferably at least 85% S-enantiomer and not more than 15% R-enantiomer, or the S-enantiomer, or a pharmaceutically acceptable salts of said racemate or enantiomer, in association with at least one pharmaceutical carrier or diluent together with instructions for the use of said pharmaceutical composition in the treatment of affective and attention disorders or anxiety or other psychiatric disorders with underlying anxiety symptomatologies.

Preferably, the racemate consists of at least 95% S-enantiomer and not more than 5% R-enantiomer, more preferably of at least 98% S-enantiomer and not more than 2% R-enantiomer, most preferably of at least 99.5% S-enantiomer and not more than 0.5% R-enantiomer The racemates of the invention can, e.g., be obtained by mixing the pure enantiomers of the compound of formula I. The pure enantiomers of the compound of formula I can be obtained starting from the racemate by procedures known as such. The racemate may be separated into its enantiomers through the formation of diastereomeric salts, for example by salt formation with an enantiomer-pure chiral acid, or by means of chromatography, for example by HPLC, using chromatographic substrates with chiral ligands.

In one embodiment of the invention, the pure enantiomers of the compound of formula I are prepared according to the procedures described in the Examples below.

The following Examples serve to illustrate the invention without limiting the invention in its scope.

| Abbreviations | |
|---|---|
| Ac | acetyl |
| aqu. | Aqueous |
| dansyl | 5-(dimethylamino)-1-naphthalenesulfonyl |
| Et | ethyl |
| HPLC | high pressure liquid chromatography |
| Me | methyl |
| NMR | nuclear magnetic resonance |
| RT | room temperature |
| THF | tetrahydrofuran |
| Ts | tosyl |

EXAMPLES

Example 1

Procedure for the Enantioselective Transfer Hydrogenation of 10-Oxo-10,11-dihydro-dibenzo[b,f] azepine-5-carboxylic acid amide to R(−)-10,11-Dihydro-10-hydroxy-5H-dibenz[b,f]azepine-5-carboxamide To a mixture of 10-oxo-10,11-dihydro-dibenzo[b,f] azepine-5-carboxylic acid amide (300 mg, 1.189 mmol) and RuCl[(1R,2R)-p-TsNCH($C_6H_5$)CH($C_6H_5$)$NH_2$]($\eta^6$-p-cymene, Aldrich, Switzerland) (8.8 mg, 0.0138 mmol) in $CH_2Cl_2$ (15 ml) is added dropwise a premixed solution of formic acid and $NEt_3$ (5:2, 328 mg:289 mg) at 23° C. and stirred for 10 min. The clear solution is heated to reflux for 16 h. The reaction mixture is cooled to RT, diluted with $CH_2Cl_2$ (20 ml) and neutralised with aqu. $NaHCO_3$. After washing with brine the solution is concentrated under reduced pressure. The residue is purified by flash chromatography on silica gel using a 6:1 EtOAc-MeOH mixture as eluent to afford of R(−)-10,11-dihydro-10-hydroxy-5H-dibenzo[b,f] azepine-5-carboxamide (enantiomeric purity (ee)>99% determined by HPLC on Chiracel OD, Retention time: 9.46 min. $[\alpha]_D^{rt}$=−195.3° (ethanol). $^1$H-NMR (400 MHz, $CDCl_3$): 7.70-7.20 (m, 8 H), 5.30 (br s,1 H), 5.10-4.60 (br s, 2 H), 3.75-3.40 (m, 1 H), 3.20-2.90 (m, 1 H), 2.50 (br s, 2 H). NMR-Datas refer to Lit.: Benes, J et al., *J. Med. Chem.* 1999, 42, 2582-2587. Molecular weight: 254.291

Example 2

Procedure for the Enantioselective Transfer Hydrogenation of 10-Oxo-10,11-dihydro-dibenzo[b,f] azepine-5-carboxylic acid amide to S(+)-10,11-Dihydro-10-hydroxy-5H-dibenz[b,f]azepine-5-carboxamide To a mixture of 10-oxo-10,11-dihydro-dibenzo[b,f] azepine-5-carboxylic acid amide (300 mg, 1.189 mmol) and RuCl[(1S,2S)-p-TsNCH($C_6H_5$)CH($C_6H_5$)$NH_2$]($\eta^6$-p-cymene) (11 mg, 0.0173 mmol) in $CH_2Cl_2$ (15 ml) is added in two portions a premixed solution of formic acid and $NEt_3$ (5:2, 656 mg:578 mg) at 23° C. and stirred for 10 min. After that formic acid is added (50 μl) and the clear solution is heated to reflux for 16 h. The reaction mixture is cooled to RT, diluted with $CH_2Cl_2$ (20 ml) and neutralised with aqu. $NaHCO_3$. After washing with brine the solution is concentrated under reduced pressure. The residue is purified by flash chromatography on silica gel using a 6:1 EtOAc-MeOH mixture as eluent to afford of S(+)-10,11-dihydro-10-hydroxy-5H-dibenzo[b,f]azepine-5-carboxamide (ee>99% by HPLC on Chiracel OD). Retention time: 12.00 min. $[\alpha]_D^{rt}$=+196.6° (ethanol). $^1$H-NMR (400 MHz, $CDCl_3$):7.70-7.20 (m, 8 H), 5.30 (br s,1 H), 5.10-4.60 (br s, 2 H), 3.75-3.40 (m, 1 H), 3.20-2.90 (m, 1 H), 2.50 (br s, 2 H). NMR-Datas refer to Lit.: Benes, J et al., *J. Med. Chem.* 1999, 42, 2582-2587. Molecular weight: 254.291

Alternative production: To a mixture of 10-oxo-10,11-dihydro-dibenzo[b,f]azepine-5-carboxylic acid amide (300 mg, 1.189 mmol) and RuCl[(1S,2S)-p-dansyl-NCH($C_6H_5$) CH($C_6H_5$)$NH_2$]($\eta^6$-p-cymene) (8.5 mg, 0.012 mmol) in $CH_2Cl_2$ (15 ml) is dropwise a premixed solution of formic acid and $NEt_3$ (5:2, 328 mg:289 mg) at 23° C. and stirred for 10 min. The clear solution is heated to reflux for 16 h. The reaction mixture is cooled to RT, diluted with $CH_2Cl_2$ (20 ml)

and neutralised with aqu. NaHCO₃. After washing with brine the solution is concentrated under reduced pressure. The residue is purified by flash chromatography on silica gel using a 6:1 EtOAc-MeOH mixture as eluent to afford of S(+)-10,11-dihydro-10-hydroxy-5H-dibenzo[b,f]azepine-5-carboxamide.

Example 3

Preparation of RuCl[(1S,2S)-p-dansylNCH($C_6H_5$)CH($C_6H_5$)NH₂]($\eta^6$-p-cymene)

a) Preparation of (S,S)-5-dimethylamino-naphthalene-1-sulfonic acid (2-amino-1,2-diphenyl-ethyl)-amide: To a solution of (S,S)-diphenylethylenediamine (250 mg, 1.2 mmol) and triethylamine (0.5 ml) in THF is added dropwise a solution of dansyl chloride (318 mg, 1.2 mmol) in THF (2 ml) at 0° C. After stirring 16 h at RT the solvent is removed in vacuum and the residue is resolved in methylenchloride (20 ml). The organic solution is washed with NaHCO₃ solution (5 ml), dried over Na₂SO₄ and after filtration the solvent is removed. Flash chromatographie afford (S,S)-5-dimethylamino-naphthalene-1-sulfonic acid (2-amino-1,2-diphenyl-ethyl)-amide as yellow oil which crystallizes by drying in vacuum. M: 445.59. ¹H-NMR (400 MHz, CDCl₃):8.36 (t, J=7.5 Hz, 2 H), 8.17 (dd, J=7.2, 1.2 Hz, 1 H), 7.47 (dd, J=8.8 Hz, 1 H), 7.34 (dd, J=8.5 Hz, 1 H), 7.24-7.16 (m, 4 H), 7.11 (d, J=7.5 Hz, 1 H), 6.99-6.74 (m, 6 H), 4.61 (d, J=8.5 Hz, 1 H), 4.20 (d, J=8.5 Hz, 1 H), 2.80 (s, 6 H).

b) Preparation of RuCl[(1S,2S)-p-dansylNCH($C_6H_5$)CH($C_6H_5$)NH₂($\eta^6$-p-cymene): A solution of (S,S)-5-dimethylamino-naphthalene-1-sulfonic acid (2-amino-1,2-diphenyl-ethyl)-amide (80 mg, 0.18 mmol), NEt₃ (36 mg, 0.36 mmol) and [RuCl₂(p-cymene)]₂ (55 mg, 0.09 mmol) in 2-propanol is heated at 80° C. for 1 h. The solvent is removed after that und the dark red residue is washed with water (2 ml). The solid is dried in vacuum and used without any purification. M: 715.34.

Example 4

Vogel Conflict Test a) Description of method: The method, which detects anxiolytic and related other psychiatric activity, follows that described by Vogel et al, Psychopharmacologia 1971; 21:1-7 Anxiolytics and antidepressants (e.g., Fontana et al., Psychopharmacology 1989; 98(2):157-62) of various classes increase punished drinking.

Rats are deprived of water for 48 hours and are then placed individually into a transparent Plexiglas enclosure (15×32×34 cm) with a floor consisting of stainless steel bars (0.4 cm) spaced 1 cm apart The back wall of the enclosure is made of opaque Plexiglass thereby concealing the observer from the experimental animal. In the centre of the opposite wall, 5 cm above the floor, a metal water spout protrudes into the cage and is connected to one pole of a shock generator (Apelex: Type 011346). The other pole of the shock generator is connected to the metal grid floor. The rat is left to explore until it found the water spout. Then, every time it drinks, it receives a slight electric shock (1.7 mA, 1 sec.) 2 seconds after it starts lapping. The number of shocks received (punished drinkings) is counted during a 3 minute period. 15 rats are studied per group. The test is performed blind. Compounds are evaluated at 50, 100 and 200 mg/kg, administered p.o. 60 minutes before the test, and compared with a vehicle control group. Clobazam (64 mg/kg), administered under the same experimental conditions, is used as reference substance. All substances are evaluated within the same experiment and compared with the same vehicle and reference substance controls. Data are analyzed by comparing treated groups with vehicle control using unpaired Student's t tests.

b) Results: The results are summarized in Tables 1-3. They clearly demonstrate that the R-enantiomer at the highest dose used (200 mg/kg) is less efficacious than the S-enantiomer at the lowest dose used (50 mg/kg), whereas the potency/efficacy ratio of the Racemate is between that of the R- and S-enantiomers. In addition, whereas the maximum efficacy of the R-enantiomer is less than that of the positive control, i.e., clobazam, the efficacy of the S-enantiomer surpasses that of clobazam at all doses tested.

TABLE 1

EFFECTS OF THE RACEMATE AND CLOBAZAM IN THE VOGEL CONFLICT TEST IN THE RAT (15 RATS PER GROUP)

| M3 | PUNISHED DRINKING (number of shocks) | | |
| --- | --- | --- | --- |
| (mg/kg) p.o. −60 min | mean ± s.e.m. | p value | % change from control |
| Vehicle | 4.4 ± 0.2 | — | — |
| 50 | 5.9 ± 0.5 * | 0.012 | +34% |
| 100 | 8.4 ± 1.0 *** | 0.001 | +91% |
| 200 | 10.4 ± 1.5 *** | 0.001 | +136% |
| CLOBAZAM 64 mg/kg p.o. −60 min | 8.2 ± 1.1 ** | 0.003 | +86% |

Student's t test: * = p < 0.05;  = p < 0.01; * = p < 0.001

TABLE 2

EFFECTS OF THE R-ENANTIOMER AND CLOBAZAM IN THE VOGEL CONFLICT TEST IN THE RAT (15 RATS PER GROUP)

| M4 | PUNISHED DRINKING (number of shocks) | | |
| --- | --- | --- | --- |
| (mg/kg) p.o. −60 min | mean ± s.e.m. | p value | % change from control |
| Vehicle | 4.4 ± 0.2 | — | — |
| 50 | 5.0 ± 0.4 NS | 0.203 | +14% |
| 100 | 5.5 ± 0.5 NS | 0.088 | +25% |
| 200 | 7.4 ± 1.3 * | 0.033 | +68% |
| CLOBAZAM 64 mg/kg p.o. −60 min | 8.2 ± 1.1 ** | 0.003 | +86% |

Student's t test: NS = Not Significant; * = p < 0.05; ** = p < 0.01

TABLE 3

EFFECTS OF THE S-ENANTIOMER AND CLOBAZAM IN THE VOGEL CONFLICT TEST IN THE RAT (15 RATS PER GROUP)

| M5 | PUNISHED DRINKING (number of shocks) | | |
| --- | --- | --- | --- |
| (mg/kg) p.o. −60 min | mean ± s.e.m. | p value | % change from control |
| Vehicle | 4.4 ± 0.2 | — | — |
| 50 | 8.4 ± 1.3 ** | 0.006 | +91% |
| 100 | 9.5 ± 1.0 *** | 0.000 | +116% |
| 200 | 10.5 ± 1.3 *** | 0.000 | +139% |
| CLOBAZAM 64 mg/kg p.o. −60 min | 8.2 ± 1.1 ** | 0.003 | +86% |

Student's t test:  = p < 0.01; * = p < 0.001

What is claimed is:

1. A method for the treatment of general anxiety disorders, social anxiety disorders, post traumatic stress disorder, obsessive compulsive disorder or panic and anxiety occurring following cessation of psychostimulant intake in a subject in need of such treatment, which comprises administering to said subject a therapeutically effective amount of a racemate of the compound of formula I,

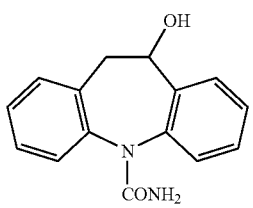

wherein said racemate consists of at least 85% S-enantiomer and not more than 15% R-enantiomer, or pharmaceutically acceptable salts thereof.

2. The method of claim 1 wherein the racemate consists of at least 95% S-enantiomer and not more than 5% R-enantiomer.

3. The method of claim 1 wherein the racemate consists of at least 98% S-enantiomer and not more than 2% R-enantiomer.

4. A method for the treatment of affective and attention disorders in a subject in need of such treatment, which comprises administering to said subject a therapeutically effective amount of a racemate of the compound of formula I

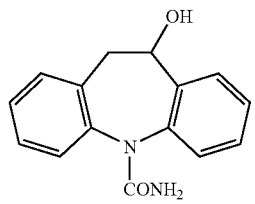

wherein said racemate consists of at least 85% S-enantiomer and not more than 15% R-enantiomer, or pharmaceutically acceptable salts thereof.

5. The method of claim 4 wherein the affective and attention disorders are bipolar disorders.

6. The method of claim 4 wherein the racemate consists of at least 95% S-enantiomer and not more than 5% R-enantiomer.

7. The method of claim 4 wherein the racemate consists of at least 98% S-enantiomer and not more than 2% R-enantiomer.

\* \* \* \* \*